(12) United States Patent
Evans et al.

(10) Patent No.: US 8,708,938 B2
(45) Date of Patent: Apr. 29, 2014

(54) LOW DENSITY MEDICAL BANDAGE SUBSTRATE, MEDICAL BANDAGE, AND MEDICAL BANDAGING PRODUCT

(75) Inventors: John C. Evans, Lancashire (GB); Shitij Chabba, Charlotte, NC (US); Martin O'Hara, Charlotte, NC (US)

(73) Assignee: BSN Medical, Inc., Charlotte, NC (US)

( * ) Notice: Subject to any disclaimer, the term of this patent is extended or adjusted under 35 U.S.C. 154(b) by 919 days.

(21) Appl. No.: 11/816,629

(22) PCT Filed: Feb. 3, 2006

(86) PCT No.: PCT/US2006/003747
§ 371 (c)(1),
(2), (4) Date: Nov. 11, 2008

(87) PCT Pub. No.: WO2006/091349
PCT Pub. Date: Aug. 31, 2006

(65) Prior Publication Data
US 2009/0054817 A1 Feb. 26, 2009

Related U.S. Application Data

(63) Continuation of application No. PCT/US2005/009017, filed on Mar. 17, 2005.

(60) Provisional application No. 60/654,172, filed on Feb. 18, 2005.

(51) Int. Cl.
| | | |
|---|---|---|
| B32B 3/00 | (2006.01) | |
| B32B 3/12 | (2006.01) | |
| B32B 3/26 | (2006.01) | |
| B21C 37/00 | (2006.01) | |
| B21H 8/00 | (2006.01) | |
| B60J 10/00 | (2006.01) | |
| B21C 27/00 | (2006.01) | |
| B32B 5/18 | (2006.01) | |
| A61F 5/00 | (2006.01) | |
| A61F 13/00 | (2006.01) | |
| A61F 13/06 | (2006.01) | |
| A61L 15/00 | (2006.01) | |

(52) U.S. Cl.
USPC ............... 602/6; 428/156; 428/159; 428/160; 428/210; 428/573; 428/594; 428/596; 428/613; 602/1; 602/2; 602/3; 602/5; 602/7; 602/8; 602/60; 602/61; 602/62; 602/63; 602/75

(58) Field of Classification Search
USPC .......... 602/1–3, 5–8, 60–63, 75–76; 428/156, 428/159, 160, 210, 219, 573, 594, 596, 613
See application file for complete search history.

(56) References Cited

U.S. PATENT DOCUMENTS 5,542,269 A * 8/1996 Richards .......................... 66/195
5,807,295 A 9/1998 Hutcheon et al.
(Continued)

*Primary Examiner* — Patricia Bianco
*Assistant Examiner* — Brandon L Jackson
(74) *Attorney, Agent, or Firm* — Shumaker, Loop & Kendrick, LLP

(57) ABSTRACT

A low density fabric substrate for a medical bandaging product. The substrate has a plurality of longitudinally-extending voids formed in the fabric for permitting water penetration through the fabric thickness from one of the major faces to the other major faces. A reactive system is impregnated into or coated onto the substrate and remains stable when maintained in substantially moisture-free conditions and hardens upon exposure to sufficient moisture to form a rigid, self supporting structure. A soft, flexible protective material covers at least one of the major faces of the substrate along its length to provide a cushioning barrier between the substrate and the skin of a patient when the material is in use.

28 Claims, 10 Drawing Sheets

(56) References Cited

U.S. PATENT DOCUMENTS

| | | |
|---|---|---|
| 6,719,710 B2 | 4/2004 | Darcey |
| 7,749,180 B2 * | 7/2010 | Chabba et al. ............... 602/8 |
| 7,972,288 B2 * | 7/2011 | Chabba et al. ............... 602/8 |
| 2002/0035343 A1 * | 3/2002 | Darcey ............... 602/8 |
| 2002/0183671 A1 | 12/2002 | Henderson et al. |
| 2004/0193083 A1 | 9/2004 | Evans et al. |

* cited by examiner

LOW DENSITY MEDICAL BANDAGE SUBSTRATE, MEDICAL BANDAGE, AND MEDICAL BANDAGING PRODUCT

TECHNICAL FIELD AND BACKGROUND OF THE INVENTION

The present invention relates generally to the field of orthopedic medicine and more specifically to the design of an improved, low density medical bandage substrate, a medical bandage formed of a moisture-curable material, particularly a splint, and a medical bandaging product.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time-consuming. Several components are required and considerable skill is necessary when applying. The hardened material is subject to deterioration during wear, is heavy and can cause odor and itching.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult.

An advance in the art of casting and splinting is disclosed in U.S. Pat. Nos. 4,411,262 and 4,502,479. The casting materials disclosed in these patents comprise a flexible fabric impregnated with a moisture-curing resin enclosed in a moisture-free, moisture-impervious package. Compared to plaster-of-paris, these products are extremely lightweight, have a very high strength to weight ratio and can be made relatively porous, permitting a flow of air through the splinting material. Prior art moisture-curing systems include a package within which is contained a plurality of layers of fabric, such as fiberglass, impregnated with a moisture-curing resin. No provision is made for re-closing the package, so that the entire material must be very quickly used after removal from the package since such moisture-curing resins will cure in a relatively short period of time due merely to contact with atmospheric moisture.

Further significant developments in the splinting area are disclosed in U.S. Pat. Nos. 4,770,299; 4,869,046; 4,899,738 and 5,003,970, owned by present applicant. Each of these patents discloses various roll-form, moisture-curable splint products that permit predetermined lengths of a medical bandage to be severed from a roll for use, while the remaining medical bandage is maintained in a soft, moisture-proof condition until ready for later use. These applications disclose the use of multiple layers of fiberglass fabric positioned in a synthetic, non-woven fabric protective layer for residing between the hardened substrate and the patient.

The present application presents and discloses further improvements addressed to presently-used products.

In particular, a double fabric substrate is disclosed having voids formed into the substrate to reduce the density of the substrate without impairing the ability of the substrate to adequately harden. The voids not only reduce the density of the substrate but form water ingress channels that permit faster, more even distribution of water into the structure of the substrate. The lower density of the substrate improves the weight ratio, the amount of water and moisture-curable resin required, improves water take-up and distribution characteristics, and provides for more even hardening of the bandage. In addition, the edges of the substrate may be formed in such a way as to be less rigid when cured, thereby improving comfort to the patient. The substrate is more formable and the lamination will not separate when wrapping around an angle, for example, heel or elbow.

The invention described in this application combine the advantages of both plaster-of-paris and moisture-curable resin systems while avoiding their respective disadvantages. This is accomplished by providing unitary splinting systems with improved strength and convenience. One such unitary system uses a moisture-curing resin together with a moisture-impervious package with means for resealing the package against entry of moisture after a desired length of bandaging product has been removed for use. In this manner, hardening of the bandaging product remaining in the moisture-impervious package is prevented thereby increasing the cost effectiveness of the system substantially. Another unitary system provides pre-cut lengths sealed against moisture intrusion until use.

SUMMARY OF THE INVENTION

It is therefore an object of the invention to provide a medical bandage substrate with improved use characteristics.

It is another object of the invention to provide a medical bandage that has a relatively low density.

It is another object of the invention to provide a medical bandage that has improved wetting and hardening characteristics.

It is another object of the invention to provide a medical bandage product in roll form with a moisture-curable resin which hardens the material upon exposure to moisture to form a rigid, self-supporting structure.

It is another object of the invention to provide a medical bandaging product which can be dispensed in any desired length while preventing hardening of the remaining material until use is desired.

It is another object of the invention to provide a medical bandage product in pre-cut lengths with a moisture-curable resin which hardens the material upon exposure to moisture to form a rigid, self-supporting structure.

It is another object of the invention to provide a medical bandage product.

It is another object of the invention to provide a unitary medical bandaging product which includes a soft, protecting wrapping to provide a cushion against the skin of a patient.

It is another object of the invention to provide a medical bandage substrate that can be incorporated into a soft, protecting wrapping after removal from its storage container and before application to the patient.

It is another object of the invention to provide a method of constructing a medical substrate having the characteristics and objects described above.

It is another object of the invention to provide a method of applying a medical bandage having the characteristics and objects described above.

These and other objects of the present invention are achieved in the preferred embodiments disclosed below by providing a low density substrate for a medical bandage, comprising an elongate fabric having two opposed major faces connected by yarns extending between the faces. The two opposed, longitudinally-extending side edges define a predetermined fabric thickness. A plurality of longitudinally-extending voids are formed in the fabric and communicate with both of the two opposed major faces for reducing the density of the substrate.

According to one preferred embodiment of the invention, the fabric comprises a warp knitted double fabric.

According to another preferred embodiment of the invention, the fabric comprises a warp knitted double fabric constructed from yarns selected from the group consisting of glass, high tenacity polyester, polypropylene, aramid, and ultra high molecular weight polyethylene.

According to yet another preferred embodiment of the invention, the yarn count range is between about 20 Tex and about 136 Tex.

According to yet another preferred embodiment of the invention, the yarn count range is between about 44 Tex and about 136 Tex.

According to yet another preferred embodiment of the invention, the fabric that forms the substrate comprises about 450-580 courses per meter and about 50-90 wales per 10 centimeters.

According to yet another preferred embodiment of the invention, the fabric thickness ranges from 1 mm to 10 mm.

According to yet another preferred embodiment of the invention, the fabric has a weight of about 500 to about 3000 grams per square meter.

According to yet another preferred embodiment of the invention, the fabric comprises a warp knitted fabric, and the voids are formed by wales omitted at intervals along the length of the substrate in one or more of a chain, inlay and center stitch of the fabric.

According to yet another preferred embodiment of the invention, one wale end is omitted at the interval of between about 2-10 wales.

According to yet another preferred embodiment of the invention, a medical bandage is provided, and comprises a low density substrate comprised of an elongate fabric having two opposed major faces connected by yarns extending between the faces, and two opposed, longitudinally-extending side edges defining a predetermined fabric thickness. A plurality of longitudinally-extending voids are formed in the fabric and communicate with both of the two opposed major faces for reducing the density of the substrate while permitting water penetration through the fabric thickness from one of the major faces to the other major faces. A reactive system is applied to and into the thickness of the substrate, the reactive system having a first state wherein the substrate remains in a flexible, conformable condition and a second state wherein the reactive system hardens, simultaneously hardening the substrate into a desired conformation.

According to yet another preferred embodiment of the invention, the reactive system comprises a moisture-curable resin, and the voids are adapted to facilitate uniform distribution of water onto and through the thickness of the substrate.

According to yet another preferred embodiment of the invention, the fabric comprises a warp knitted double fabric constructed from yarns selected from the group consisting of glass, high tenacity polyester, polypropylene, aramid, and ultra high molecular weight polyethylene, and including a moisture-curable reactive system applied to and into the thickness of the substrate, and wherein the voids are adapted to facilitate uniform distribution of water onto and through the thickness of the fabric.

According to yet another preferred embodiment of the invention, the medical bandage includes a soft, flexible protective material covering at least one of the major faces of the substrate and adapted to pass water therethrough and onto the substrate.

According to yet another preferred embodiment of the invention, the substrate is in a precut length suitable for a particular medical use.

According to yet another preferred embodiment of the invention, the substrate is in the form of a roll from which desired lengths may be cut as needed.

According to yet another preferred embodiment of the invention, a low density medical bandaging product is provided, and comprises a sleeve formed of moisture-impervious material and sealable to prevent entry of moisture, and a medical material positioned in the sleeve and sealed therein against entry of moisture until use. The medical material comprises a low density substrate formed of an elongate fabric having two opposed major faces connected by yarns extending between the faces, and two opposed, longitudinally-extending side edges defining a predetermined fabric thickness. A plurality of longitudinally-extending voids are formed in the fabric and communicate with both of the two opposed major faces for reducing the density of the substrate while at the same time permitting improved water penetration through the fabric thickness from one of the major faces to the other major faces. A reactive system is impregnated into or coated onto the substrate. The system remains stable when maintained in substantially moisture-free conditions and hardens upon exposure to sufficient moisture to form a rigid, self supporting structure. A soft, flexible protective material covers at least one of the major faces of the substrate along its length to provide a cushioning barrier between the substrate and the skin of a patient when the material is in use.

According to yet another preferred embodiment of the invention, the product includes a soft, flexible protective material covering both major faces of the substrate.

According to yet another preferred embodiment of the invention, the product includes a soft, flexible protective material wrapped around and enclosing both major faces and the longitudinally extending side edges of the substrate.

According to yet another preferred embodiment of the invention, the fabric comprises a warp knitted double fabric.

According to yet another preferred embodiment of the invention, the fabric comprises a warp knitted double fabric constructed from yarns selected from the group consisting of glass, high tenacity polyester, polypropylene, aramid, and ultra high molecular weight polyethylene.

According to yet another preferred embodiment of the invention, the fabric comprises a warp knitted fabric, and further wherein the voids are formed by wales omitted at intervals along the length of the substrate in one or more of a chain, inlay and center stitch of the fabric.

According to yet another preferred embodiment of the invention, one wale end is omitted at the interval of between about 2-10 wales.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIG. 4 is a perspective view of a medical bandage substrate according to one embodiment of the invention;

DESCRIPTION OF THE PREFERRED EMBODIMENTS AND BEST MODE

Figure 1:
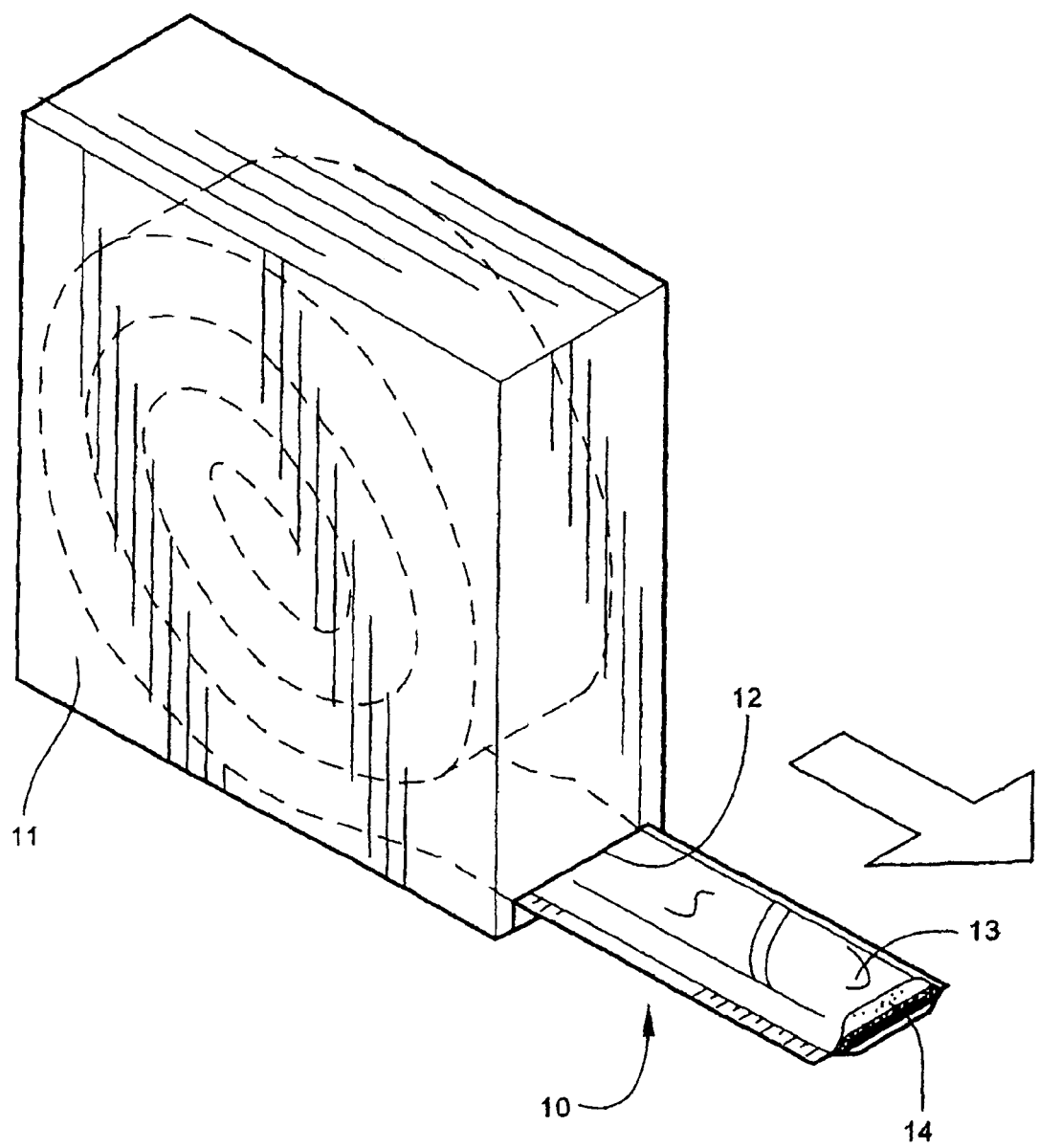
FIG. 1 is a perspective view showing a medical bandaging product according to one preferred embodiment of the invention being dispensed from a dispenser.

Referring now specifically to the drawings, a medical bandaging product according to the present invention is shown generally in FIG. 1 at 10. Bandaging product 10 may be sold in any convenient length, such as 24 feet, and is rolled into a coil and positioned in a suitable dispenser 11. Dispenser carton 11 is provided with a slot 12 at one lower corner through which bandaging product 10 is dispensed.

According to one embodiment of the invention, the bandaging product 10 is formed of an outer elongate sleeve 13 formed of a moisture-impervious material, for example, a laminated metal foil and plastic. Sleeve 13 is heat sealed along opposite, parallel extending sides to form an elongate tube. An elongate medical bandage 14, described in detail below, is positioned within sleeve 13 and is maintained in substantially moisture-free conditions until dispensed. The medical bandage 14 is dispensed by pulling the needed amount of material, along with the sleeve 13 in which it is enclosed, out of the carton 11 and severing it with, for example, scissors. The remaining, raw end of the bandage 14 is tucked back into the remaining sleeve 13 with a sufficient length of sleeve available to receive a clip, such as a bar clip. Of course, any suitable form of closure may be used so long as a seal sufficient to prevent moisture intrusion is formed.

Figure 2:
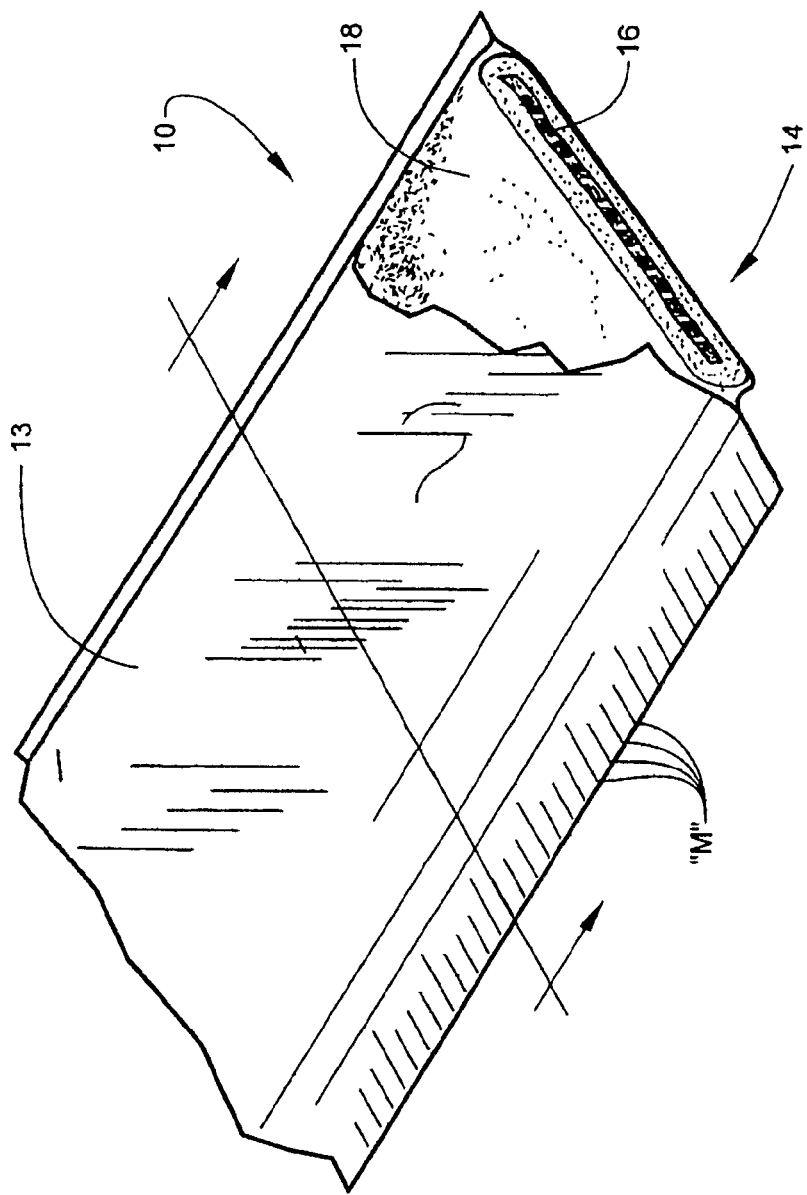
FIG. 2 is a perspective view with parts broken away of a cut length of medical bandage.

Referring now to FIG. 2, since the appropriate length of bandage 14 is best determined by measurement, measurement marks "M" are printed on one edge of the sleeve 13. The sleeve 13 is preferably closely conforming to the bandage 14 along its length in order to reduce the amount of air that is introduced into the sleeve while it is open.

Figure 3:
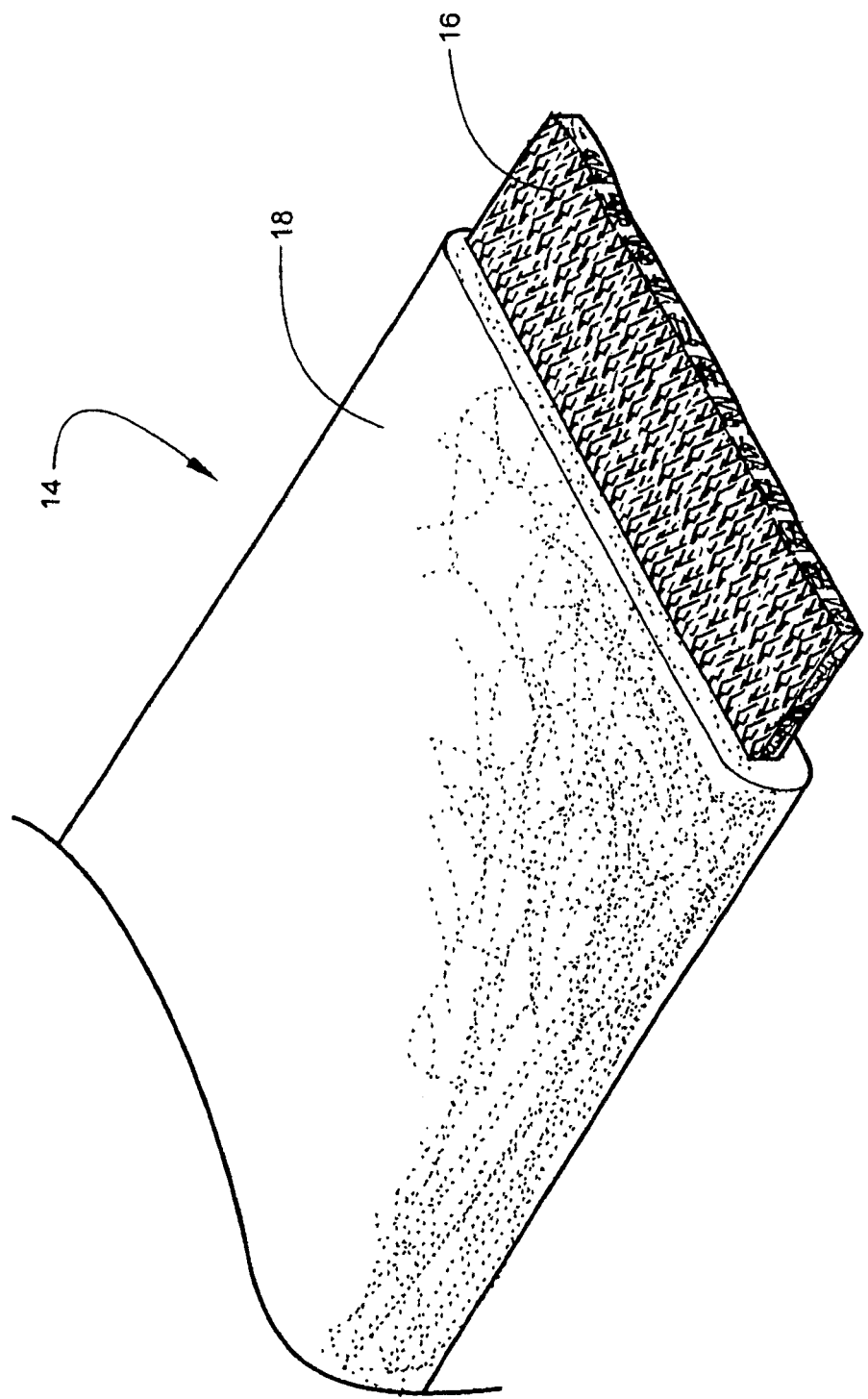
FIG. 3 is a vertical cross-section taken substantially along lines 3-3 of FIG. 2.
Figure 4:
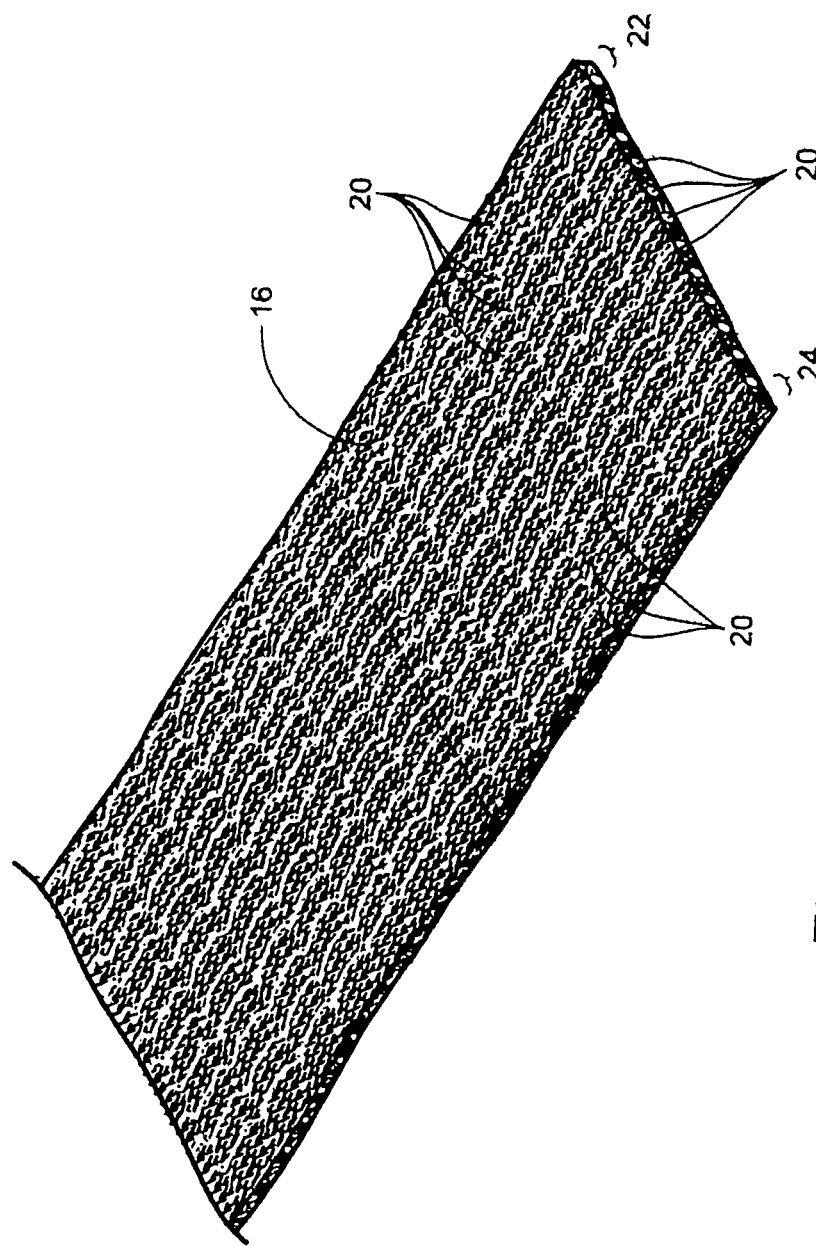
FIG. 4 is a perspective view of a length of the medical material with the low density substrate layer exposed for clarity.

Referring now to FIGS. 3 and 4, bandage 14 comprises a low density substrate 16 preferably formed of a double fabric of a material, which may be woven, knitted or formed according to other processes, as described in further detail below. According to one embodiment of the invention the substrate 16 is contained within a tubular wrapping 18 that is preferably formed of a soft, flexible non-woven fiber such as polypropylene or some other suitable fiber. This provides a cushioning protective layer between the skin of the patient and substrate 16.

The wrapping 18 may also be selected from a wide range of other materials such as open cell or reticulated foam, closed cell foam, soft flexible films and nonwoven materials. In the preferred form the splint is wrapped in a nonwoven material.

Alternatively, the substrate 16 may be packed in the sleeve 13 and enclosed within a protective cushioning layer just before application. This may be accomplished by folding a length of cushioning material around the substrate 16 and securing it in place with, for example, tape or another form of adhesive.

Substrate 16 is impregnated or coated with a reactive system which remains stable when maintained in substantially moisture-free conditions but which hardens upon exposure to sufficient moisture to form a rigid, self-supporting structure. Two typical formulations of the reaction system is set forth in the following tables:

TABLE 1

| Isonate ↓ 143L | or | | |
|---|---|---|---|
| Mondur ↓ CD | or | polyisocyanate | 50.0% |
| Rubinate ↓ XI168 | | | |
| Pluracol ↓ P1010 | | polyol | 46.6% |
| DC-200 Silicone | | defoaming agent | 0.30% |
| Benzoyl Chloride | | stabilizer | 0.10% |
| Thancat. DM-70 | | catalyst | 3.0% |
| | | | 100% |

TABLE 2

| Isonate 143L | or | | |
|---|---|---|---|
| Mondur CD | or | Polysiocyanate | 50.0% |
| Carbowax PEG 600 | | | |
| Carbowax PEG 4600 | | | 22.0% |
| Carbowax PEG 8000 | | | |
| Voranol 230-238 | | | |
| Voranol 220-110 | | | 18.0% |
| Irganox 1010 | | | 2.0% |
| Antifoam 1400 | | | 4.0% |
| Methane Sulphonic Acid | | | 1.0% |
| DMDEE | | | 3.0% |
| | | | 100% |

These formulations and their varying proportions are well-known.

By continued reference to FIG. 4, the substrate 16 according to one embodiment is formed of a single layer of a knitted double fabric impregnated with a resin, for example, one of the moisture-curable resins identified above, but also may utilize a wide range of available polymer chemistries, including but not limited to polyurethanes, polyureas, polyesters, polyacrylates and epoxy. In one of the preferred embodiments the splint comprises a warp knitted double fabric impregnated with a moisture curable polyurethane resin. The warp knitted double fabric can be constructed using any suitable organic or inorganic yarns/fibers such as glass, high tenacity polyester, polypropylene, aramid fibers (Kevlar®) and ultra high molecular weight polyethylene (Spectra®). The yarn count ranges are preferably between 20 Tex to 136 Tex and preferably 44 Tex to 136 Tex. The warp knitted double fabric formed a three-dimensional substrate 16 having a top and a bottom layer that are interconnected using plurality of yarns. The yarns used for forming the top layer, bottom layer and the interconnection between them can be constructed from same or different materials.

In one of the preferred embodiments, the substrate material is knitted on a double bed warp knitted machine with six guide bars. The preferred fabric notation is an inlay with a chain stitch on the surface and a "V," butterfly or atlas stitch in the center. The yarns are knitted into a three-dimensional fabric substrate having sufficient weight and thickness to keep the resin within the substrate.

The fabric structure can be tailored for any level of course and wales density. However, in the preferred construction, the fabric that forms the substrate 16 comprises 450-580 courses per meter, with a preferred range of 500-550 courses per meter and 50-90 wales per 10 centimeters, with a preferred range of 65-75 wales per 10 centimeters, and a most preferred value of 70 wales per 10 centimeters. The fabric can be constructed into any suitable width for varying limb sizes and shapes. The most preferred knitted fabric widths vary in the range of 2.5 centimeters to 60 centimeters. The fabric thickness is an important feature as it effects the final rigidity and is also important aesthetically for patient's comfort and ease of use. The warp knitted fabric in this embodiment can vary in thickness range from 1 mm to 10 mm and preferably in the range of 2 mm to 5 mm. The final fabric weight will depend on various factors such as fabric construction, yarns used and other factors that are well known in the prior art. In the most preferred structure the fabric weight will vary in the range of 500 to 3000 grams per square meter and even more preferably in the range of 1000 to 1800 gram per square meter.

According to one preferred embodiment of the invention, fiberglass yarns are used to construct the single layer fabric. Fiberglass possesses certain advantages because of its low cost and the experience developed over years of use in conventional fiberglass splints. It has been learned that particular advantages result when a substrate fabric having the channels 20 is heat treated after knitting and before application of the moisture-curable resin.

In particular, heating the knitted substrate 16 incrementally to a relatively high temperature over a period of hours sufficient to burn off processing starch and then reducing the temperature over a period of hours to ambient temperature enables the resin to more securely and evenly coat the fiberglass filaments.

In one preferred process, the knitted fiberglass substrate is treated by slowly heating in stages to 400° C. over a period of hours, holding the temperature at 400° C. for 6 hours, and gradually reducing the temperature in stages to ambient temperature, the total processing time being approximately 24 hours. The improved resin adherence results from the removal of the starch coating from the surface of the fiberglass yarns, allowing the more efficient dispersion of the resin throughout the glass knitted structure.

However, it has also been observed unexpectedly that water penetration into the substrate 16 is also enhanced by heat treating as described above. This is believed to also be the result of the removal of the starch layer, which may total approximately 3 percent of the total product volume. Removal of the starch layer reduces the diameter of the individual yarns, thereby increasing the open space between adjacent yarns. The cumulative effect is to increase by approximately 3 percent the volume of the openings in the substrate 16, thereby increasing the area available for resin penetration and, ultimately water ingress for the purpose of curing, not only in the channels 20 but throughout the length, width and thickness of the substrate 16.

The resulting improvement in performance has been demonstrated in testing heat treated knitted substrate material and comparable non-heat treated substrate material. In one such test, resin was applied to non-heat treated knitted fiberglass substrate material at a rate sufficient to achieve a 36 percent resin content. The resin was activated by water and the strength of the substrate observed at subsequent time intervals. Strength, observed as the kilograms of force required to deform the substrate one centimeter according to a standard test, was >1.29 after 15 minutes and >1.82 after 30 minutes. The greater value after 30 minutes reflects continued hardening between 15 and 30 minutes, thereby requiring greater force to achieve the required one centimeter deformation.

In contrast, resin was applied to the same knitted fiberglass substrate material after heat treatment to remove the starch coating. As with the non-heat treated material, the resin was applied at a rate sufficient to achieve a 36 percent resin content. The resin was activated by water and strength of the substrate observed at subsequent time intervals. Strength, observed as the kilograms of force required to deform the substrate one centimeter according to a standard test, was >2.29 after 15 minutes and >2.08 after 30 minutes. The greater value after 15 minutes reflects a more rapid hardening in the first 15 minutes, a highly desirable result. The overall hardness after 15 and 30 minutes is considered to be generally the same. As shown, the strength of the heat treated substrate is greater in both absolute terms and in the speed with which hardening occurs than with non-heat treated substrate.

Testing also revealed that the strength of the heat treated substrate increased at 24 hours to 3.31, or over 50 percent greater than the required minimum strength of greater than 2.0.

Figure 5:
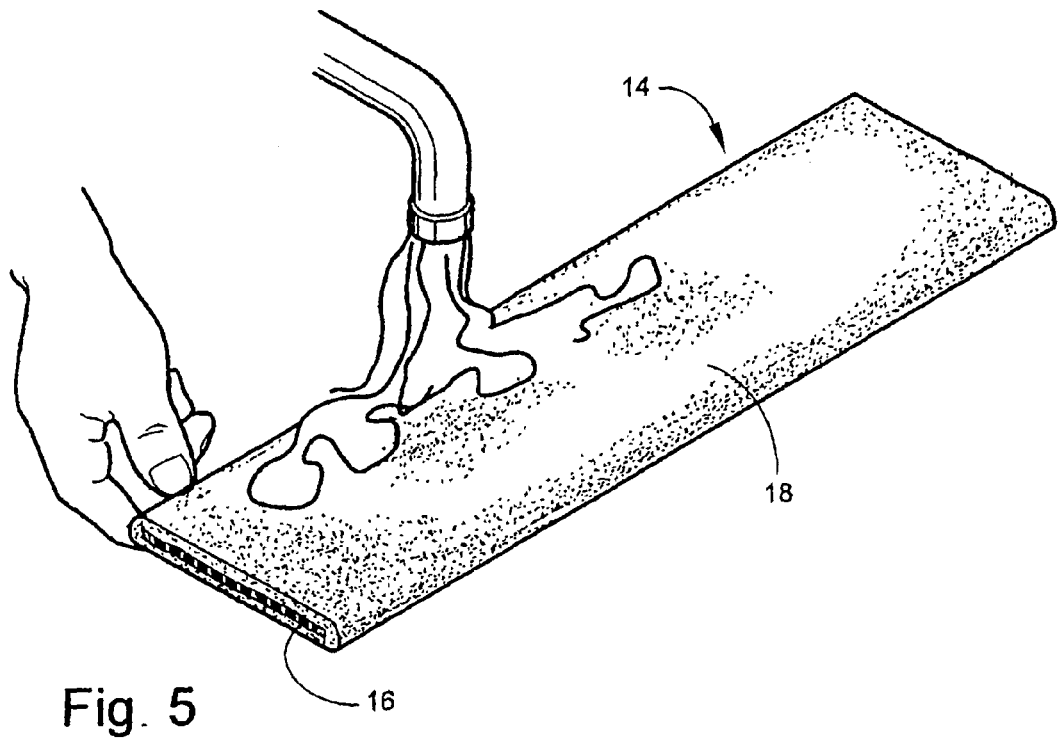
FIG. 5 illustrates activation of the moisture-curable resin in the medical material by wetting.
Figure 6:
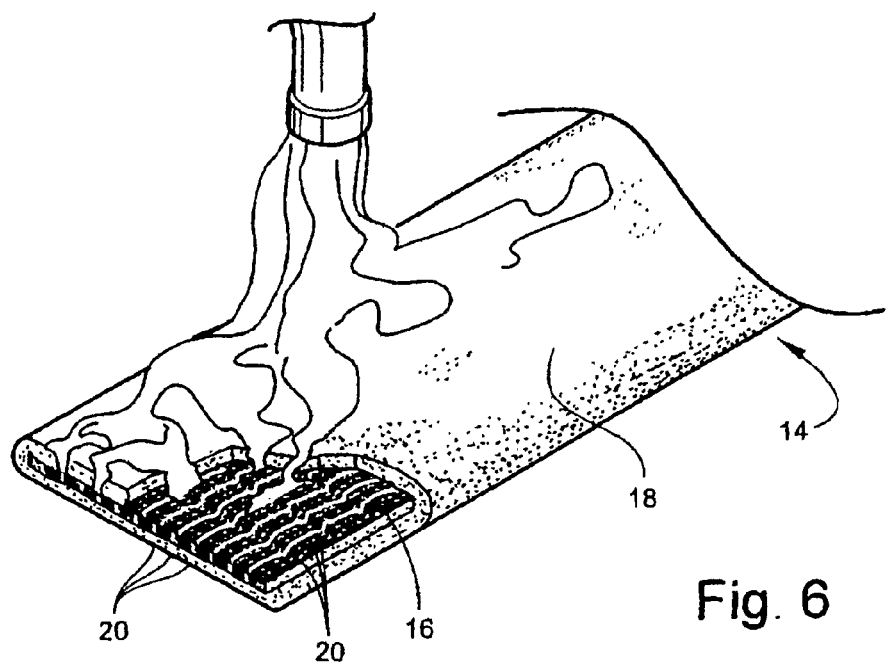
FIG. 6 further illustrates activation of the moisture-curable resin by providing water flow into the voids in the substrate.
Figure 7:
FIG. 7 shows excess water being removed from the medical bandage before application.
Figure 8:
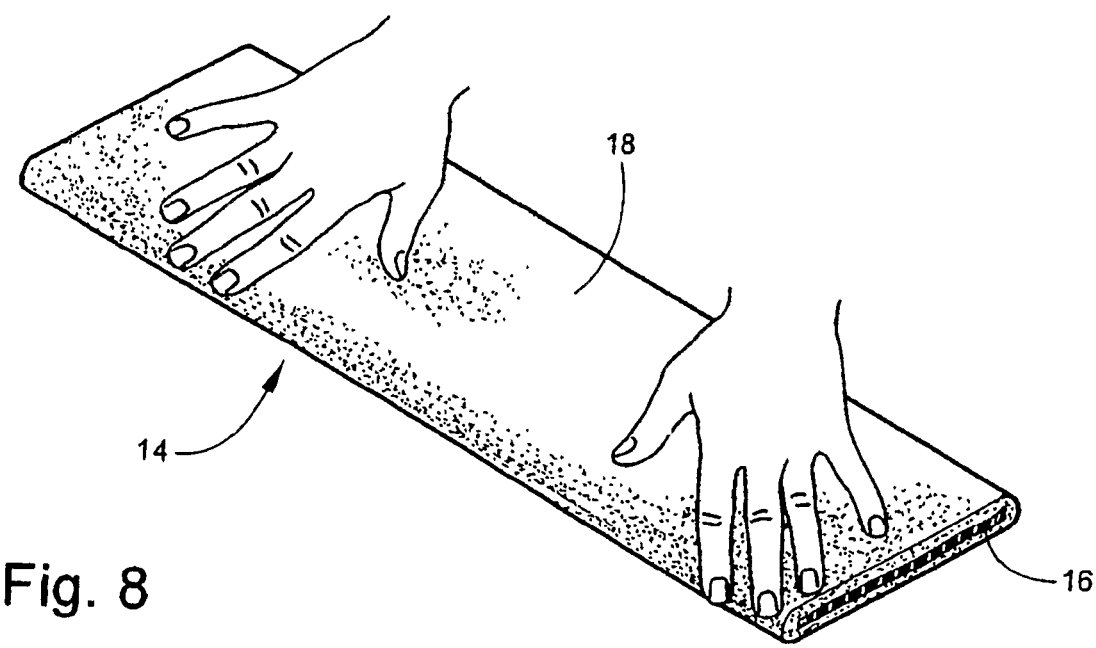
FIG. 8 shows smoothing and straightening of the medical bandage before application.

As is shown in FIGS. 5-8, the bandage 14 is typically activated by spraying or pouring water on one surface of the bandage 14, FIGS. 5 and 6, wringing out the excess water, FIG. 7, and smoothing the bandage before application, FIG. 8.

It is desirable that the bandage 14 activates and attains rigidity sufficient to hold the fracture in position as fast as possible.

One of the factors influencing the rate of rigidification is the openness of the substrate structure to allow water to penetrate through the thickness of the bandage—both the wrapping 18 and the substrate 16—and activation of the whole bandage 14 evenly and rapidly. In one preferred embodiment the substrate 16 is knitted in according to a method by which a wale is omitted from the knitted structure at a regular interval along the length of the substrate 16 in either the chain, inlay or center stitch. In the most preferred embodiment a wale end is omitted every 2-10 wales. The missing wale ends create voids 20 that extend along the length and into the thickness of the substrate 16, thus reducing the density of the substrate 16 and allowing for faster and more even penetration of water into the structure of the substrate 16, as is shown schematically in FIG. 6. The actual configuration of the voids 20 is a function of the type of fabric formation technique utilized, and the shape and size of the void areas are defined by surrounding yarns or fibers. The low density substrate 16 is desirable in that raw material and weight are reduced, at least to some degree. Alternative methods for creating the voids 20 include omitting stitches or yarns in the width direction of the substrate, or diagonally across and along the substrate, the principal point being to reduce the weight and density of the substrate 16, while providing greater opportunity for water ingress into the structure of the substrate 16, rather than any one particular method of doing so.

In accordance with another embodiment of the invention, the "V" stitch should preferably be formed using a textured, filamented or fibrillated yarn that improves the density of the center portion of the double fabric, thereby improving the resin-retaining capacity of the material.

This aspect of performance enhances long term use or storage life of the product, avoiding the resin leaching or bleeding out of the double fabric into the padding layer so making the product unfit for use.

In accordance with another embodiment of the invention, substrate 16 is formed with soft longitudinally extending side edges 22, 24.

As is also shown particularly in FIGS. 4 and 6, the soft side edge areas 22, 24 are created by introducing a softer, low modulus yarn such as polyester, polyethylene and polypropylene at the edges of the substrate 16. These side edge areas 22, 24 may be formed of 1 to 15 wales, preferably 7 wales per inch and even more preferably 4 wales. In addition, a more open knitted structure may be incorporated into the side edges 22, 24 to further reduce the stiffness of the substrate 16 in these marginal areas.

Figure 9:
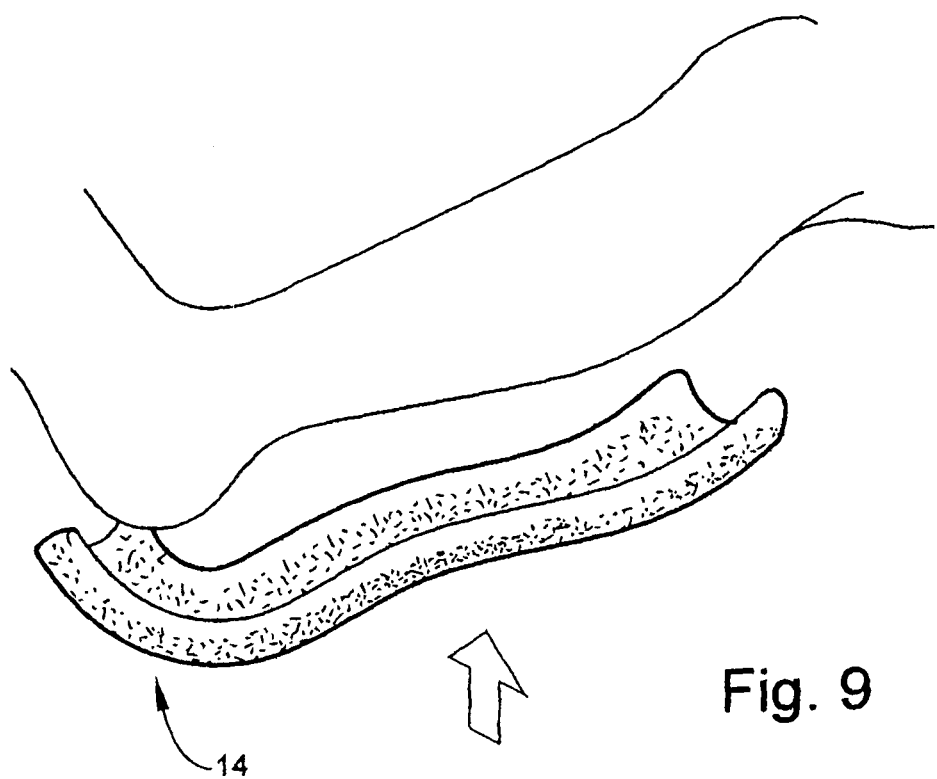
FIGS. 9 and 10 are perspective views of the medical bandage being placed on an injured limb and being secured into place by a covering wrap.
Figure 10:
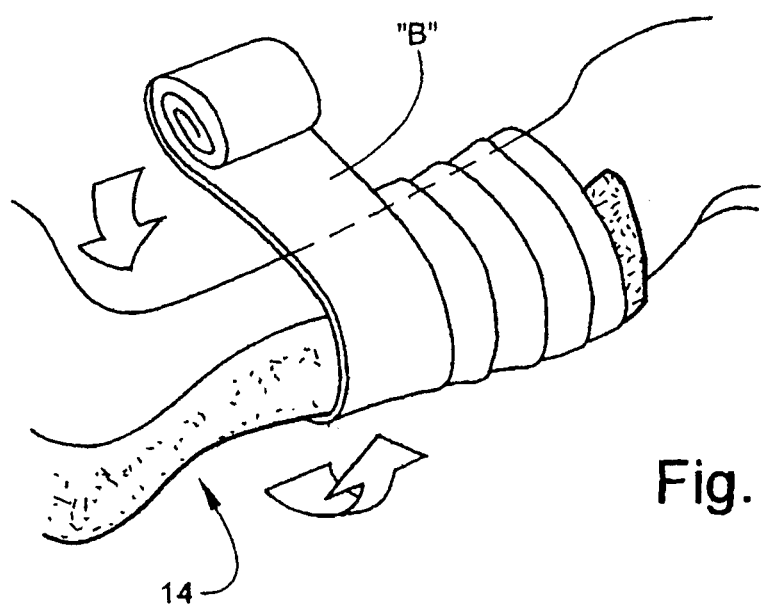

Referring now to FIG. 9, an appropriate length of material 14 is formed to the shape of the body member to be immobilized. This particular type of splint, known as a posterior short leg splint, is formed by molding a length of the product 14 to the calf and up over the heel and onto the foot. Then, product 14 is overwrapped with an elastic conventional bandage "B", as is shown in FIG. 10.

Figure 11:
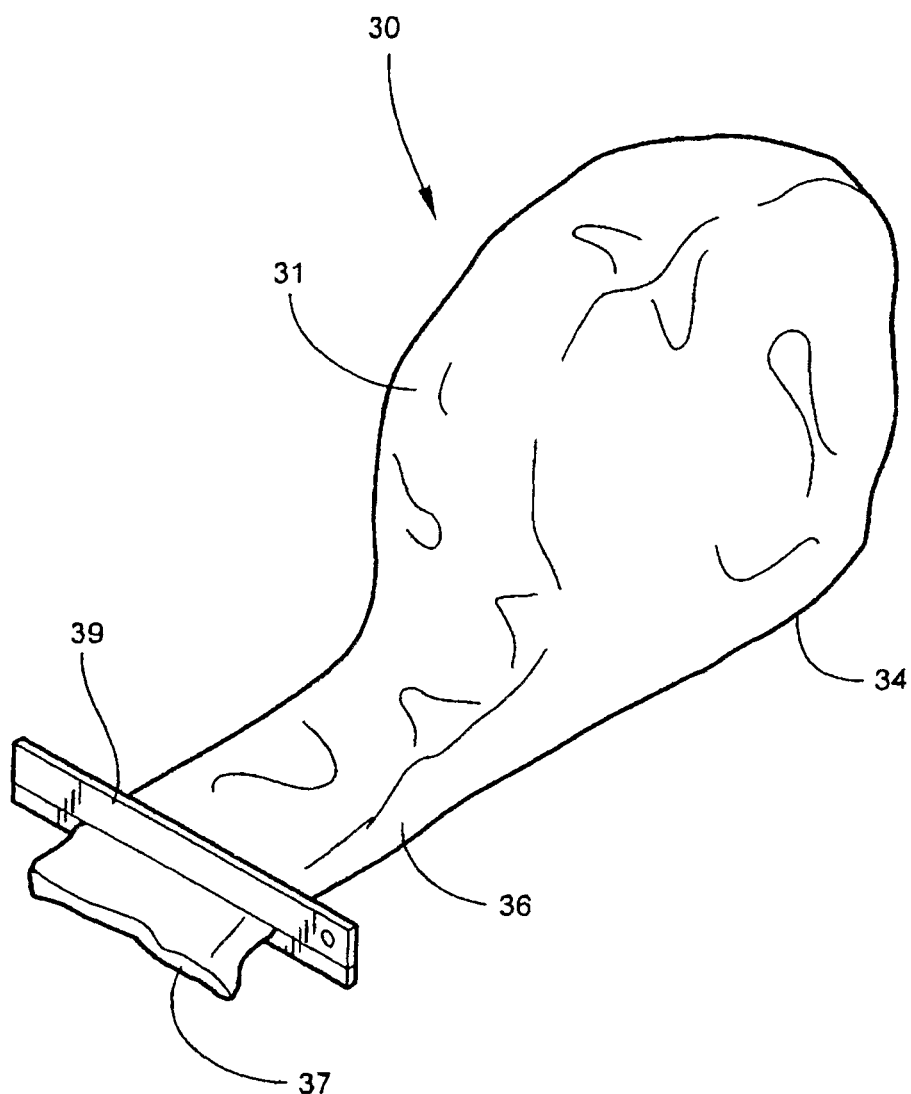
FIG. 11 is a perspective view of an alternative design of a dispensing container for holding the medical bandage until ready for dispensing.
Figure 12:
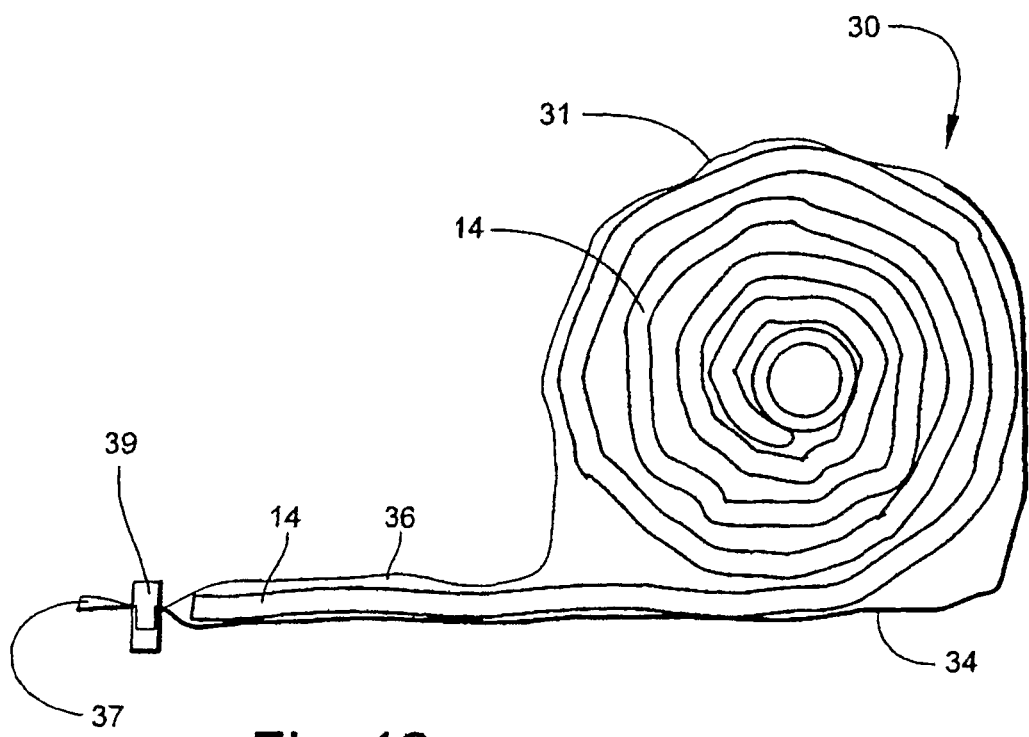
FIG. 12 is a vertical cross-section of the dispensing container shown in FIG. 11.
Figure 13:
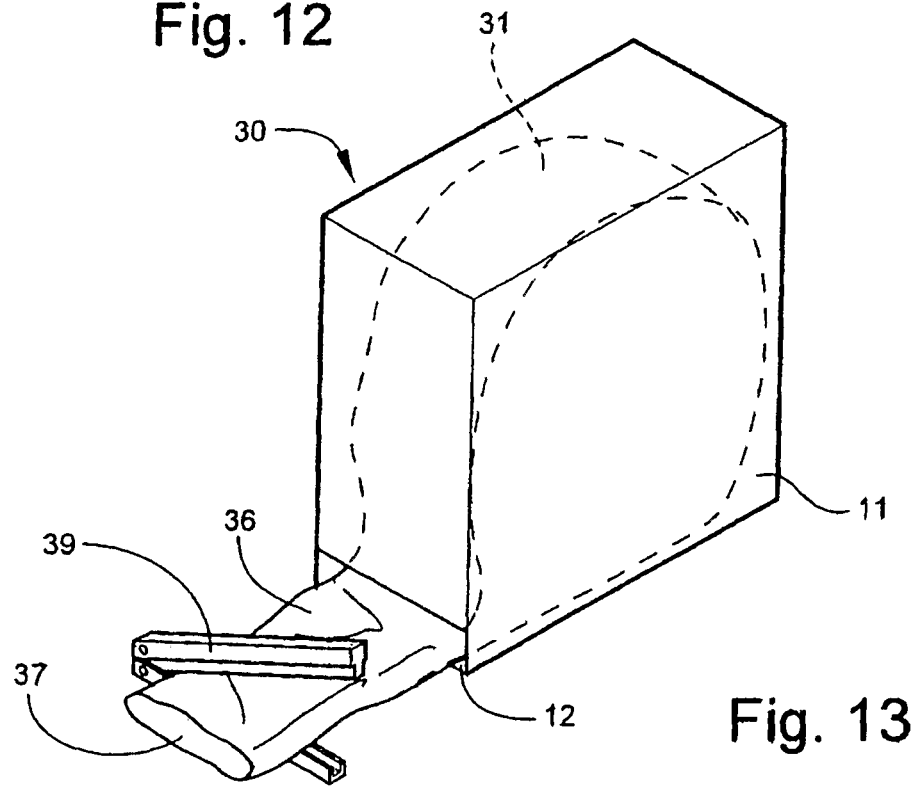
FIG. 13 is a perspective view of the dispenser carton into which the container is positioned.

Referring now to FIGS. 11-13, a medical bandaging product according to another embodiment of the invention is shown at broad reference numeral 30. The medical bandage 14 is positioned within a container 31 which is formed of two laminated elongate sheets placed in registration and heat sealed along a common seam to form a moisture proof container of the same material and construction as the sleeve 13. The outer layer is formed of a tear-resistant plastic film and the middle layer comprises aluminum foil and acts as a moisture barrier. The inner layer is a plastic film having thermoplastic properties suitable for heat sealing the interior of container 31 securely against moisture.

As is also shown in FIG. 11, container 31 includes an enlarged product storage package 34 in which is contained a coil of the medical bandage 14. Package 34 is integral and communicates with an elongate dispensing sleeve 36 having an openable end 37 through which the medical bandage 14 in the container 31 is dispensed.

As is shown in FIGS. 12 and 13, the end 37 of dispensing sleeve 32 may be sealed with a clamp of any suitable type, such as a bar clamp 39, or any other suitable closure.

Figure 14:
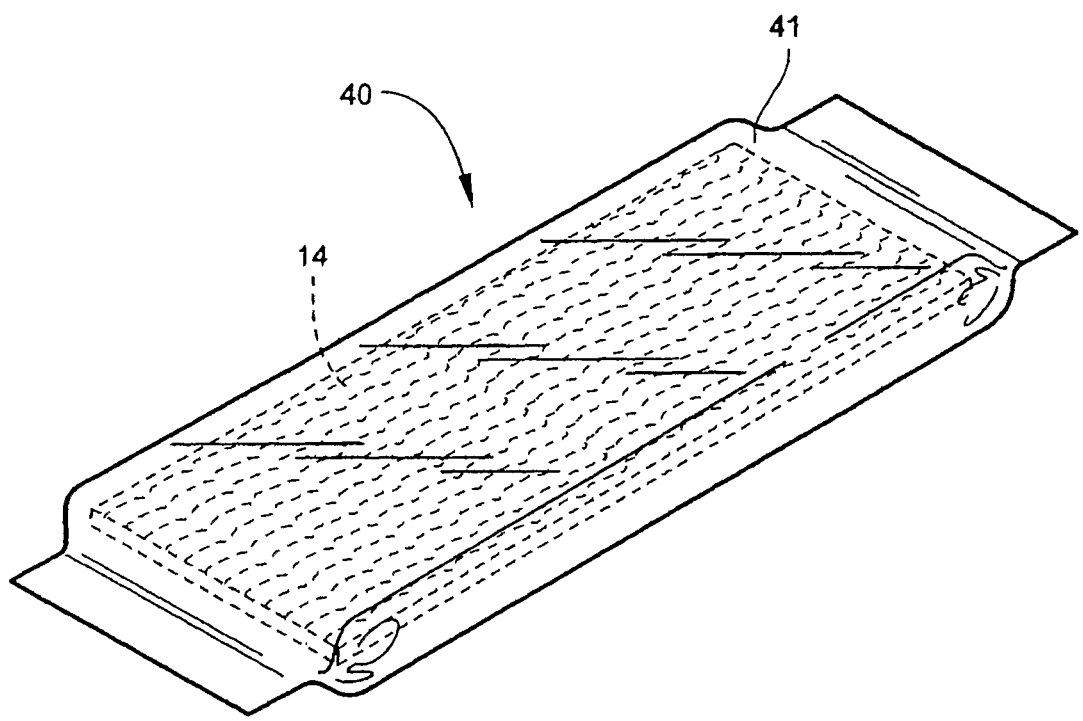
FIG. 14 is a perspective view of a pre-cut medical bandage stored for use in a moisture-impervious envelope until ready for use.

As is shown in FIG. 12, dispensing sleeve 36 fits snugly around the medical material 14 in order to limit exposure of the medical material 14 to air which enters when the opening 37 is unsealed for dispensing the medical bandage 14. FIG. 14 also shows that the medical material 14 is coiled into a relatively tight coil to limit exposure to air and sealed into the container 31. When opening 37 is properly sealed, container 31 is sufficiently airtight so that medical material 14 remains in its soft, uncured state for much longer than the usual length of time needed to exhaust the supply of medical material 14 in container 31. If a short length of the medical material 14 adjacent the opening 37 hardens, it can be cut away and discarded.

A desired length of medical material 14 is dispensed by removing clamp 39 and grasping the exposed end of the medical material 14. The appropriate length is pulled out of container 31—the medical material 14 uncoiling in the storage package 34. When the proper length has been dispensed through opening 37, it is cut and the end is tucked back into the dispensing sleeve 36. The open end 37 is quickly resealed.

As is shown in FIG. 13, if desired, the medical bandaging product 30 can be placed inside a dispensing carton 11, with the dispensing sleeve 32 of container 31 projecting out of the slot 12 in the bottom of carton 11.

Referring now to FIG. 14, a pre-cut embodiment of a medical bandage product is shown. The medical bandage product 40 comprises a moisture-impervious envelope 41 in which is packaged a pre-cut length of the medical bandage 14, preferably having the structure and characteristics described above with reference to FIGS. 1-13. The medical bandaging product 40 is sized according to the desired end use and is labeled as such. The medical bandage 14 may be removed from the envelope 41 and used as is, or cut and shaped as needed to meet the medical requirements of the treating physician and technician.

We claim:

1. A low density substrate for a medical bandage, comprising:
   (a) a heat-treated elongate fabric having two opposed major faces connected by yarns extending between the faces, and two opposed, longitudinally-extending side edges defining a predetermined fabric thickness; and
   (b) a plurality of longitudinally-extending voids formed in the fabric and communicating with both of the two opposed major faces for reducing the density of the substrate while maintaining sufficient mass to harden into a rigid structure upon activation of a reactive system;
   wherein the fabric comprises a warp knitted fabric and the density reducing voids are formed by wales omitted at intervals along the length of the substrate in one or more of a chain, inlay and center stitch of the fabric and stitches omitted in the width direction of the substrate when viewed in the length direction of the substrate; and
   wherein the major faces and longitudinally-extending side edges of the substrate are covered with a tubular cushioning material constructed of non-woven material adapted to pass water therethrough to the substrate, and the cushioning material and the substrate together form a unitary medical bandaging product; and
   wherein the longitudinally-extending side edges include one or more low modulus yarn selected from the group consisting of polyester, polyethylene and polypropylene.

2. A substrate according to claim 1, wherein the fabric comprises a warp knitted double fabric constructed from yarns selected from the group consisting of glass, high tenacity polyester, polypropylene, aramid, and ultra high molecular weight polyethylene.

3. A substrate according to claim 2, wherein the yarn count range is between about 20 Tex and about 136 Tex.

4. A substrate according to claim 2, wherein the yarn count range is between about 44 Tex and about 136 Tex.

5. A substrate according to claim 2, wherein the fabric that forms the substrate comprises about 450-580 courses per meter and about 50-90 wales per 10 centimeters.

6. A substrate according to claim 1, wherein the fabric comprises a warp knitted double fabric.

7. A substrate according to claim 1, wherein the fabric thickness ranges from 1 mm to 10 mm.

8. A substrate according to claim 1, wherein the fabric has a weight of about 500 to about 3000 grams per square meter.

9. A substrate according to claim 1, wherein one wale end is omitted at the interval of between about 2-10 wales.

10. A medical bandage according to claim 1, wherein the substrate is in the form of a roll from which desired lengths may be cut as needed.

11. A low density medical bandage, comprising:
(a) a heat-treated substrate comprised of an elongate fabric having two opposed major faces connected by yarns extending between the faces, and two opposed, longitudinally-extending side edges defining a predetermined fabric thickness;
(b) a plurality of longitudinally-extending voids formed in the fabric and communicating with both of the two opposed major faces for reducing the density of the substrate; and
(c) a reactive system applied to and into the thickness of the substrate, the reactive system having a first state wherein the substrate remains in a flexible, conformable condition and a second state wherein the reactive system hardens, simultaneously hardening the substrate into a desired conformation;
wherein one wale end is omitted from the fabric every 2-10 wales and stitches are omitted in the width direction of the substrate when viewed in the length direction of the substrate for reducing the density of the substrate; and
wherein the major faces and longitudinally-extending side edges of the substrate are covered with a tubular cushioning material constructed of non-woven material adapted to pass water therethrough to the substrate, and the cushioning material and the substrate together form a unitary medical bandaging product; and
wherein the longitudinally-extending side edges include one or more low modulus yarn selected from the group consisting of polyester, polyethylene and polyproplyene.

12. A medical bandage according to claim 11, wherein the reactive system comprises a moisture-curable resin, and wherein the voids are also adapted to facilitate uniform distribution of water onto and through the thickness of the substrate.

13. A medical bandage according to claim 11, wherein the fabric comprises a warp knitted double fabric constructed from yarns selected from the group consisting of glass, high tenacity polyester, polypropylene, aramid, and ultra high molecular weight polyethylene, and including a moisture-curable reactive system applied to and into the thickness of the substrate, and wherein the voids are adapted to facilitate uniform distribution of water onto and through the thickness of the fabric.

14. A medical bandage according to claim 11, and including a soft, flexible protective material covering at least one of the major faces of the substrate and adapted to pass water therethrough and onto the substrate.

15. A medical bandage according to claim 11, wherein the fabric is selected from the group consisting of woven, non-woven and knitted.

16. A medical bandage according to claim 11, wherein the fabric thickness ranges from 1 mm to 10 mm.

17. A medical bandage according to claim 11, wherein the substrate is in a precut length suitable for a particular medical use.

18. A low density medical bandaging product, comprising:
(a) a sleeve formed of moisture-impervious material and sealable to prevent entry of moisture;
(b) a medical material positioned in the sleeve and sealed therein against entry of moisture until use, the medical material comprising:
(i) a heat-treated substrate formed of an elongate fabric having two opposed major faces connected by yarns extending between the faces, and two opposed, longitudinally-extending side edges defining a predetermined fabric thickness, the longitudinally-extending side edges including one or more low modulus yarn selected from the group consisting of polyester, polyethylene and polypropylene;
(ii) a plurality of longitudinally-extending voids formed in the fabric and communicating with both of the two opposed major faces and stitches omitted in the width direction of the substrate when viewed in the length direction of the substrate for reducing the density of the substrate;
(c) a reactive system impregnated into or coated onto the substrate, the system remaining stable when maintained in substantially moisture-free conditions and hardening upon exposure to sufficient moisture to form a rigid, self supporting structure; and
(d) a soft, flexible protective material covering at least one of the major faces of the substrate along its length to provide a cushioning barrier between the substrate and the skin of a patient when the material is in use;
wherein the fabric comprises a warp knitted fabric and the ingress channels are formed by wales omitted at intervals along the length of the substrate in one or more of a chain, inlay and center stitch of the fabric.

19. A medical bandaging product according to claim 18, wherein the fabric comprises a warp knitted double fabric constructed from yarns selected from the group consisting of glass, high tenacity polyester, polypropylene, aramid, and ultra high molecular weight polyethylene.

20. A medical bandaging product according to claim 19, wherein the yarn count range is between about 20 Tex and about 136 Tex.

21. A medical bandaging product according to claim 19, wherein the yarn count range is between about 44 Tex and about 136 Tex.

22. A medical bandaging product according to claim 19, wherein the fabric that forms the substrate comprises about 450-580 courses per meter and about 65-75 wales per 10 centimeters.

23. A medical bandaging product according to claim 19, wherein the fabric thickness ranges from 1 mm to 10 mm.

24. A medical bandaging product according to claim 19, wherein the fabric has a weight of about 500 to about 3000 grams per square meter.

25. A medical bandaging product according to claim 19, wherein one wale end is omitted at the interval of between about 2-10 wales.

26. A medical bandaging product according to claim 18, and including a soft, flexible protective non-woven material covering both major faces and longitudinally-extending side edges of the substrate, the non-woven material and the substrate together forming a unitary bandaging product.

27. A medical bandaging product according to claim 18, and including a soft, flexible protective material wrapped around and enclosing both major faces and the longitudinally extending side edges of the substrate.

28. A medical bandaging product according to claim 18, wherein the fabric comprises a warp knitted double fabric.

* * * * *